(12) United States Patent
Hawkes

(10) Patent No.: US 7,842,071 B2
(45) Date of Patent: Nov. 30, 2010

(54) TRANSVERSE CONNECTOR

(75) Inventor: David T. Hawkes, Pleasant Grove, UT (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 11/776,449

(22) Filed: Jul. 11, 2007

(65) Prior Publication Data

US 2008/0015588 A1   Jan. 17, 2008

Related U.S. Application Data

(60) Provisional application No. 60/830,177, filed on Jul. 11, 2006.

(51) Int. Cl.
*A61B 17/70* (2006.01)
(52) U.S. Cl. ..................................... 606/252
(58) Field of Classification Search .......... 606/250–253
See application file for complete search history.

(56) References Cited

U.S. PATENT DOCUMENTS

| | | | |
|---|---|---|---|
| 2,638,391 A | 5/1953 | Smith | |
| 3,499,222 A | 3/1970 | Linkow et al. | |
| 4,611,582 A | 9/1986 | Duff | |
| 4,641,636 A | 2/1987 | Cotrel | |
| 4,773,402 A | 9/1988 | Asher et al. | |
| 4,957,495 A | 9/1990 | Kluger | |
| 5,002,542 A | 3/1991 | Frigg | |
| 5,005,562 A | 4/1991 | Cotrel | |
| 5,024,213 A | 6/1991 | Asher et al. | |
| 5,030,220 A | 7/1991 | Howland | |
| 5,084,049 A | 1/1992 | Asher et al. | |
| 5,102,412 A | 4/1992 | Rogozinski | |
| 5,129,900 A | 7/1992 | Asher et al. | |
| 5,133,716 A | 7/1992 | Plaza | |
| 5,147,359 A | 9/1992 | Cozad et al. | |
| 5,154,718 A | 10/1992 | Cozad et al. | |
| 5,176,680 A | 1/1993 | Vignaud et al. | |
| 5,196,013 A | 3/1993 | Harms et al. | |
| 5,275,600 A | 1/1994 | Allard et al. | |
| 5,304,179 A | 4/1994 | Wagner | |
| 5,312,405 A | 5/1994 | Korotko et al. | |
| 5,330,473 A | 7/1994 | Howland | |
| 5,334,203 A | 8/1994 | Wagner | |
| 5,368,594 A | 11/1994 | Martin et al. | |

(Continued)

FOREIGN PATENT DOCUMENTS

EP    1093761    4/2001

(Continued)

OTHER PUBLICATIONS

International Search Report, PCT/US07/73283.

*Primary Examiner*—Thomas C Barrett
*Assistant Examiner*—Michael J Araj
(74) *Attorney, Agent, or Firm*—Fitch, Even, Tabin & Flannery

(57) ABSTRACT

A crosslink or connecting assembly is provided to secure multiple spinal rods in relation to each other. The connecting assembly is disposed transversely between two spinal rods and has moveable components for rotating, pivoting, and extending portions of the connecting device in order to accommodate the positioning of the spinal rods.

32 Claims, 10 Drawing Sheets

U.S. PATENT DOCUMENTS

| | | |
|---|---|---|
| 5,403,316 A | 4/1995 | Ashman |
| 5,423,818 A | 6/1995 | Van Hoeck et al. |
| 5,439,463 A | 8/1995 | Lin |
| 5,443,465 A | 8/1995 | Pennig |
| 5,470,333 A | 11/1995 | Ray |
| 5,498,263 A | 3/1996 | DiNello et al. |
| 5,522,816 A | 6/1996 | Dinello et al. |
| 5,527,314 A | 6/1996 | Brumfield et al. |
| 5,531,745 A | 7/1996 | Ray |
| 5,531,747 A | 7/1996 | Ray |
| 5,569,246 A | 10/1996 | Ojima et al. |
| 5,584,831 A | 12/1996 | McKay |
| 5,601,552 A | 2/1997 | Cotrel |
| 5,609,592 A | 3/1997 | Brumfield et al. |
| 5,624,442 A | 4/1997 | Mellinger et al. |
| 5,630,816 A | 5/1997 | Kambin |
| 5,643,262 A | 7/1997 | Metz-Stavenhagen et al. |
| 5,662,653 A | 9/1997 | Songer et al. |
| 5,667,507 A | 9/1997 | Corin et al. |
| 5,683,393 A | 11/1997 | Ralph |
| 5,688,272 A | 11/1997 | Montague et al. |
| 5,707,372 A | 1/1998 | Errico et al. |
| 5,709,684 A | 1/1998 | Errico et al. |
| 5,709,685 A | 1/1998 | Dombrowski et al. |
| 5,810,819 A | 9/1998 | Errico et al. |
| 5,910,142 A | 6/1999 | Tatar |
| 5,928,232 A | 7/1999 | Howland et al. |
| 5,947,966 A * | 9/1999 | Drewry et al. ............... 606/252 |
| 5,947,967 A | 9/1999 | Barker |
| 5,980,521 A | 11/1999 | Montague et al. |
| 5,980,523 A | 11/1999 | Jackson |
| 5,984,922 A | 11/1999 | McKay |
| 5,997,539 A | 12/1999 | Errico et al. |
| 6,063,089 A | 5/2000 | Errico et al. |
| 6,083,226 A | 7/2000 | Fiz |
| 6,096,039 A | 8/2000 | Stoltenberg et al. |
| 6,110,173 A | 8/2000 | Thomas, Jr. |
| 6,113,600 A | 9/2000 | Drummond et al. |
| 6,126,660 A | 10/2000 | Dietz |
| 6,136,003 A | 10/2000 | Hoeck et al. |
| 6,139,548 A | 10/2000 | Errico |
| 6,171,311 B1 | 1/2001 | Richelsoph |
| 6,179,838 B1 | 1/2001 | Fiz |
| 6,217,578 B1 | 4/2001 | Crozet et al. |
| 6,234,705 B1 * | 5/2001 | Troxell ........................ 403/237 |
| 6,238,396 B1 | 5/2001 | Lombardo |
| 6,261,288 B1 | 7/2001 | Jackson |
| 6,264,658 B1 | 7/2001 | Lee et al. |
| 6,283,967 B1 | 9/2001 | Troxell et al. |
| 6,302,882 B1 | 10/2001 | Lin et al. |
| 6,328,740 B1 | 12/2001 | Richelsoph |
| 6,402,751 B1 | 6/2002 | Hoeck et al. |
| 6,413,258 B1 | 7/2002 | Bernhardt et al. |
| 6,432,108 B1 | 8/2002 | Burgess et al. |
| 6,468,276 B1 | 10/2002 | McKay |
| 6,488,682 B2 | 12/2002 | Kikuchi et al. |
| 6,524,310 B1 * | 2/2003 | Lombardo et al. ........... 606/250 |
| 6,554,832 B2 * | 4/2003 | Shluzas ...................... 606/252 |
| 6,602,253 B2 * | 8/2003 | Richelsoph et al. ......... 606/252 |
| 6,692,500 B2 * | 2/2004 | Reed ........................... 606/300 |
| 6,866,664 B2 | 3/2005 | Schar et al. |
| 2002/0143330 A1 * | 10/2002 | Shluzas ...................... 606/61 |
| 2002/0169448 A1 * | 11/2002 | Vanacker ..................... 606/61 |
| 2003/0114852 A1 * | 6/2003 | Biedermann et al. ......... 606/61 |
| 2003/0114853 A1 * | 6/2003 | Burgess et al. ............... 606/61 |
| 2005/0080416 A1 * | 4/2005 | Ryan et al. ................... 606/61 |
| 2005/0107789 A1 * | 5/2005 | Sweeney ...................... 606/61 |
| 2006/0116687 A1 * | 6/2006 | Miller et al. .................. 606/73 |
| 2006/0206114 A1 * | 9/2006 | Ensign et al. ................. 606/61 |
| 2006/0271051 A1 * | 11/2006 | Berrevoets et al. ........... 606/61 |
| 2008/0109039 A1 * | 5/2008 | Michielli et al. ............. 606/251 |

FOREIGN PATENT DOCUMENTS

| | | |
|---|---|---|
| EP | 1138267 | 10/2001 |
| EP | 1302169 | 4/2003 |
| WO | 2002017803 | 3/2002 |
| WO | 2002030307 | 4/2002 |
| WO | 2006055914 | 5/2006 |
| WO | WO 2006/055914 A2 * | 5/2006 |

* cited by examiner

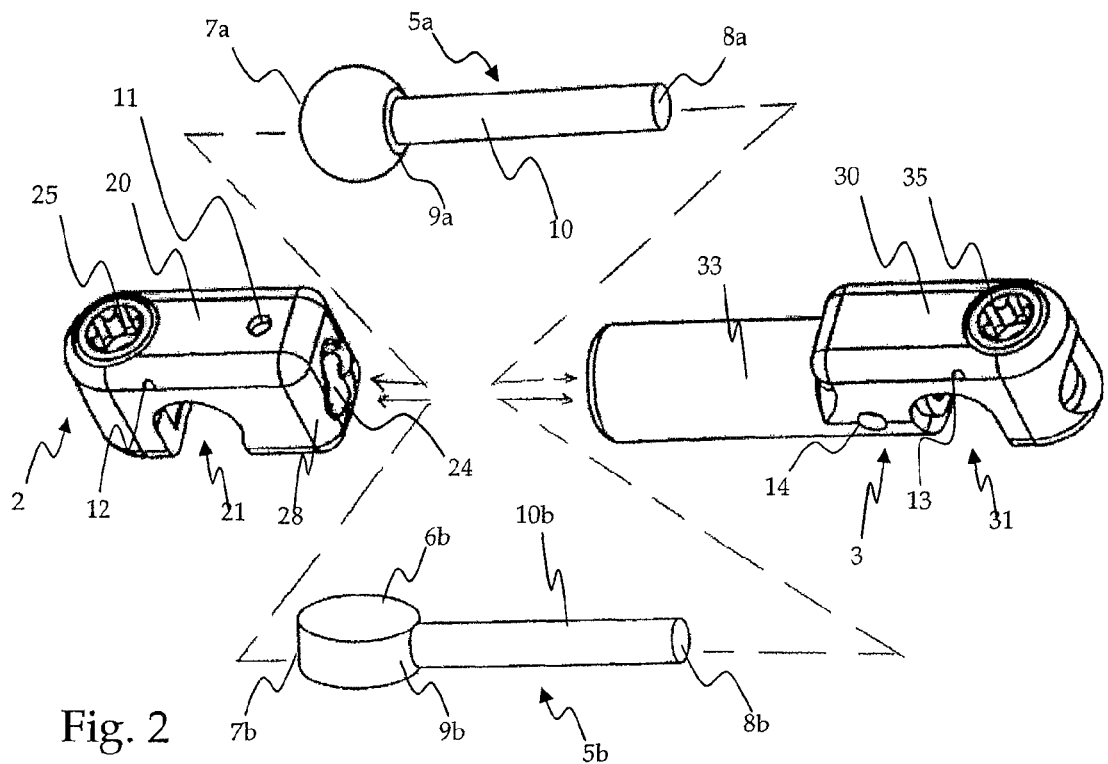
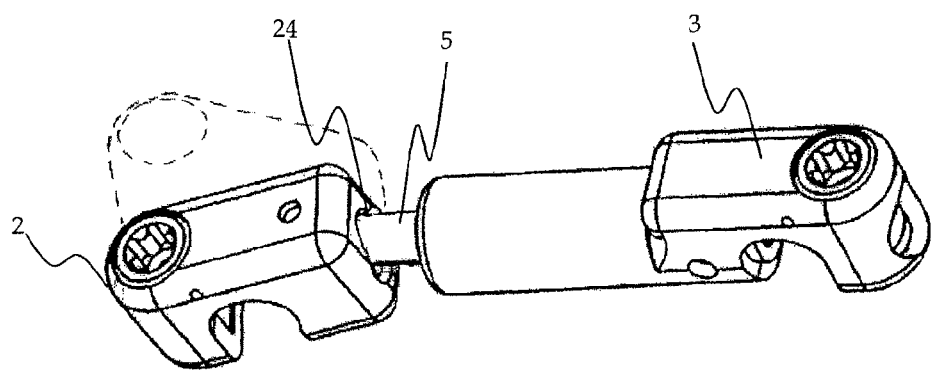
Fig. 2
Fig. 3

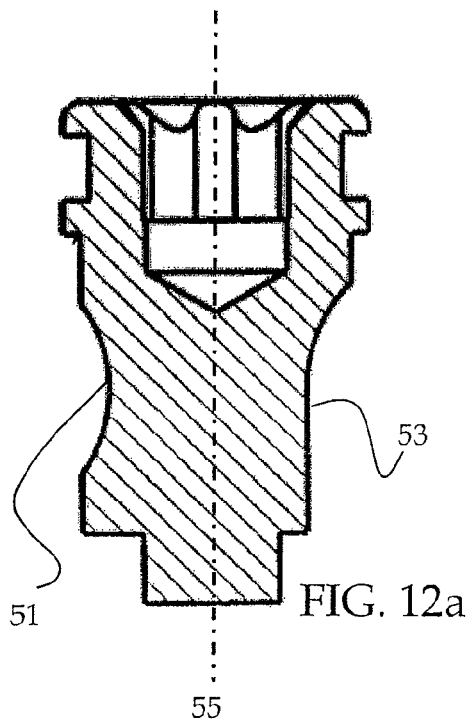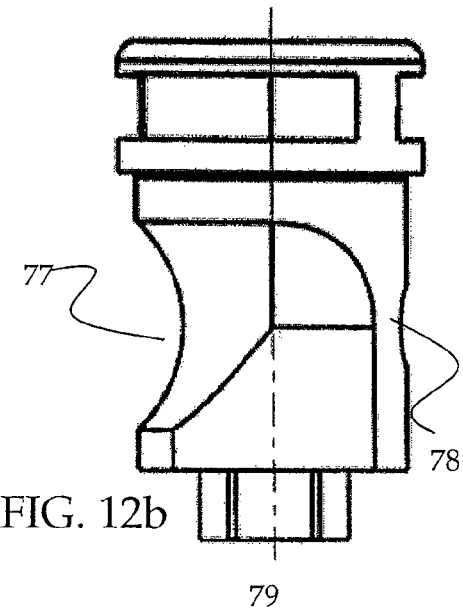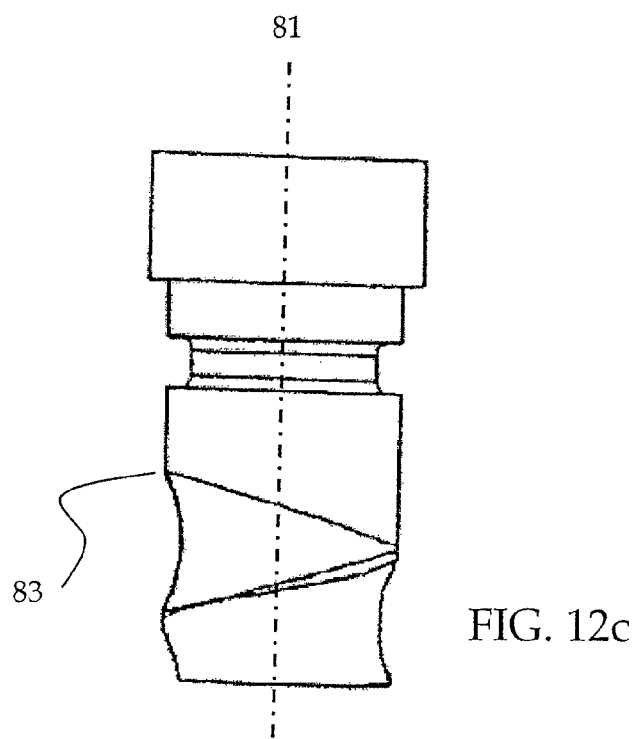

132  130  131

TRANSVERSE CONNECTOR

FIELD OF THE INVENTION

The invention relates to a crosslink or connecting assembly and method to secure multiple spinal rods in relation to each other and, in particular, to a connecting assembly disposed transversely between two spinal rods that has moveable components for rotating, pivoting, and extending portions of the connecting device, as well as actuating members for locking the moveable components in place.

BACKGROUND OF THE INVENTION

In surgical procedures involving the spine, it is common to secure a pair of spinal rods to a series of vertebrae so that the rods are aligned essentially parallel to the spinal column. The spinal rods may serve to immobilize vertebrae, preventing unwanted flexion, extension, and rotation of vertebrae with respect to each other. It is often further desirable, or even necessary, to provide a connecting device to extend transversely between spinal rods, thereby securing the spinal rods relative to each other.

Spinal rods are typically anchored to the vertebrae via bone screws that extend through the pedicle into the vertebral bodies or by hooks that engage about the vertebrae. The spinal rods are connected to the screws or anchor members by coupling members designed to receive and secure a rod. For instance, the coupling member may be yoke-shaped with a cap to close and lock the open end of the yoke. Such coupling members may be integral with the anchor member, or may be provided as a separate component in order to allow for polyaxial movement of the anchor member.

Surgical procedures involving the spine benefit from minimal invasiveness of the surgery and from having a low-profile for any fixtures secured in the body. While incisions are required during such surgical procedures in order to gain access to the site where the implant is secured, such incisions can cause damage, injury, and trauma to the patient's body. To avoid causing unnecessary damage, it is preferable to make the incisions as small and as few as possible. The ease of recovery and mobility of a patient with spinal fixtures is greatly influenced by the invasiveness of the procedure and by the size of any spinal fixtures. To this end, minimally invasive surgery systems (MISS) have been developed to minimize trauma to the patient, such as the system described in WO 06091863, the subject matter of which is hereby incorporated by reference as if fully set forth herein, wherein in certain embodiments a docking sleeve is inserted into a small incision to provide a portal through which the implantation procedure may be performed. Such a docking sleeve may also have docking fasteners in order to fix the docking sleeve to bone during the surgical procedure.

When utilizing crosslinking or connecting devices to secure pedicle screws, a number of obstacles are commonly encountered. Spinal rods are mounted by a surgeon in a custom-fit manner, including some bending of the rod, so that the rod extends properly along the spine for holding the vertebral portions in proper relation. Accordingly, there is often not a predetermined distance between two spinal rods, and the rods may converge or diverge from each other. In addition, one spinal rod may have a portion directed at an angle or curve different from that of the other rod. Therefore, the central axes of the two spinal rods may be skewed, pivoted, or rotated relative to each other.

One attempt at overcoming these obstacles and to facilitate linking of non-parallel portions of spinal rods is a crosslinking system that includes two opposed ends comprising clamping devices for securing the spinal rods, with the clamping devices linked to each other by a central cross rod or rods, typically allowing three degrees of movement. That is, the central cross rod is attached to the connecting devices in a manner that provides articulation points that allow (i) adjustment of the distance between the connector ends by axial movement of the cross rod; (ii) pivotal adjustment of at least one connecting device about one end of the cross rod; and (iii) rotation of the connecting devices relative to each other about the axis of the cross rod.

However, providing multiple points of articulation presents further problems. For instance, the components of the cross connector must be configured in such a way that they do not interfere with each other when arranged in various configurations. Furthermore, each articulation point must be capable of locking in order to secure the spinal rods in a desired configuration, requiring multiple locking mechanisms that must be loosened and tightened in order to adjust and secure the cross connector. Additionally, cross connectors with multiple points of articulation and multiple locking mechanisms are often difficult to implement in MISS applications, since the surgeon must gain access to each of the locking mechanisms, which in many transverse connector systems are located on the cross rod portion traversing the gap between the two spinal rods. Thus, the surgeon must make additional incisions at points between the implanted spinal rods in order to adjust and secure the cross connector.

Furthermore, it is common for the connecting ends of a transverse connector to have a hook portion extending around a spinal rod and pointing back towards the center of the transverse connector for securing to a spinal rod. In such an arrangement, installation or implantation of the device requires clearance laterally of the spinal rods so that the hook portion can be placed outside of the spinal rod and then drawn inward for securing the rod. Often, the patient's soft tissue must be cleared for this purpose, a result which may exacerbate pain, discomfort, and healing time.

In addition, many connecting members utilize set screws. For instance, set screws may be utilized for securing the hook portion to the spinal rod, and a set screw may be utilized for securing one connector end relative to the other. A set screw generally only provides a line or point contact with the surface against which it is driven. When a set screw drives against a spinal rod or other fixture, damage and distortion may occur at the interface. This can lead to uneven securement by the set screw, localized weakening of the fixture, loosening of the screw, or debris ground from either the screw or the fixture. Additionally, the screws require a threaded path long enough to provide a secure hold for the screw, which adds to the material cost, to the size of the fixture, and to the invasiveness of the procedure. Use of set screws also often requires use of a torque driver to insure that the screws are not over-tightened.

Moreover, the use of a set screw in the central fastening area presents a danger to the patient. The connecting member spans the dura portion of the spine. Put simply, portions of the spine other than bone, such as the discs or even the spinal cord itself, may be exposed. Use of a driver to tighten set screws on the transverse connector exposes the non-bone spinal portions to damage caused by the driver slipping from the set screw and punching into the discs or spinal cord in, for instance, in awl-like fashion.

Accordingly, there has been a need for an improved transverse connector for securing spinal rods relative to each other.

SUMMARY OF THE INVENTION

A transverse connecting assembly is provided for interconnecting spinal rods that are secured to vertebrae. The connecting assembly comprises a cross rod having a first end and a second end, a first rod receiving device positioned at the first end of the cross rod for receiving a first spinal rod, a second rod receiving device for receiving a second spinal rod at the second end of the cross rod, and one or more points of articulation for allowing linear movement, pivotal movement, and/or rotational movement of the cross rod and one rod receiving device with respect to the other rod receiving device. Each rod receiving device further includes an actuator.

In one form, a connecting assembly comprises a first rod receiving device for receiving a first spinal rod and having a first actuator member, a second rod receiving device for receiving a second spinal rod and having a second actuator member, and a cross rod connecting the first and second rod receiving devices. One or both of the actuator members may be configured to shift a spinal rod toward the cross rod. For instance, at least one of the actuators may be a rotatable cam member that shifts an adjacent spinal rod radially outward from the rotational axis of the actuator.

In another form, rotation of one of the actuators secures one of the cross rod ends against pivoting relative to the associated rod receiving device, and rotation of the other actuator secures the opposite end of the cross rod against axial shifting relative to the other rod receiving device.

In another form, operating the actuators secures the spinal rods to the transverse connecting assembly and simultaneously locks the points of articulation within the connector assembly, preventing relative movement of the rod receiving devices and spinal rods.

In yet another form, a first spinal rod is seated in a first rod receiving device, a second spinal rod is seated in a second rod receiving device, and the rods are shifted toward each other in the respective first and second rod receiving devices to fully lock the first spinal rod, second spinal rod, and the cross rod via said shifting of the spinal rods toward each other to substantially fix the spinal rods and cross rod linear, rotational, and pivotal movement with respect to the first and second rod receiving devices.

In another form, a connecting assembly for interconnecting spinal rods comprising rod receiving devices connected by a cross rod, wherein at least one of the rod receiving devices includes an arcuate seat and a rotatable actuator, the rotatable actuator having a shank including a helical cam surface configured to cause shifting of a spinal rod along the helical shank surface toward the arcuate seat as the actuator is rotated.

In another form, a connecting assembly for interconnecting spinal rods comprises two rod receiving devices connected by a cross rod, wherein the rod receiving devices include seats for receiving spinal rods and actuator members located adjacent the seats, wherein the actuator members each have a locking face rotatable into engagement with the adjacent spinal rod to shift the spinal rod for generating a locking force that fixes the cross rod against movement relative to the associated rod receiving device in a predetermined direction. The locking force further may be either directly or indirectly applied by the spinal rod to the cross rod.

In another form, a connecting assembly for interconnecting spinal rods comprising two rod receiving devices connected by a cross rod includes at least one seat for receiving a spinal rod and at least one actuator member having a locking face, wherein contacting the locking face to the spinal rod received in the seat drives the spinal rod into locking engagement with an end of the cross rod to fix both the spinal rod and the cross rod against movement relative to at least one of the rod receiving devices.

In one aspect, the first and second rod receiving devices may have rotatable actuator members that apply a locking force upon an adjacent spinal rod. The actuator member and spinal rod may be arranged so that the locking force pushes the spinal rod into engagement with an end of the cross rod, locking the cross rod into position. Alternatively, the actuator may be positioned between the cross rod and spinal rod so that a first side of the actuator locks against the spinal rod while a second side of the actuator locks against the cross rod. The actuators may also be of a non-rotational type. For instance, actuators may be provided that pivot or translate into a locking position to engage a spinal rod and/or the cross rod.

One or both ends of the cross rod may be configured for articulation. The actuators serve to lock these points of articulation, preventing movement of the cross rod relative to the rod receiving device housing the actuator. In one aspect, a first rod receiving device has a first rotatable actuator member and an opening for pivotably receiving the first end of a cross rod, while the second rod receiving device has a second rotatable actuator member and an opening slidably and rotatably receiving a second end of the cross rod so that the second end of the cross rod may be shifted to an adjusted depth and rotated about its axis within the second rod receiving device. In one form, manipulating the first actuator member simultaneously secures a first spinal rod within the first rod receiving device and locks the first end of the cross rod against pivotal movement, while manipulation of the second actuator member simultaneously secures the second spinal rod within the second rod receiving device and locks the second end of the cross rod against axial and rotational movement. In this manner, operating only two actuator members is effective to fully lock the first spinal rod, second spinal rod, and the cross rod, thereby preventing linear, rotational, and pivotal movement of the spinal rods and cross rod with respect to the first and second rod receiving devices.

In order to lock the spinal rods and cross rod, the actuators may be formed as generally asymmetric members that are rotatably mounted to the rod receiving devices. For instance, the actuators may be configured so that a cross section of the actuator perpendicular to the actuator's axis of rotation taken at a level where the actuator engages the spinal rod during operation has at least one surface point that is further from the axis of rotation than at least one other surface point. The cross section therefore may be any shape that is not rotationally symmetrical, such as elliptical, oblong, rectangular, irregular, and the like. The cross section may also be circular, as long as the axis of rotation does not pass through the center of the circle. Preferably the actuator does not have sharp corners in cross section, so that it may transition smoothly from an unlocked position to a locked position without having sharp edges engaged with the spinal rods, which may cut into the rod as pressure is applied.

Asymmetric rotatable actuators as described herein are asymmetric with respect to at least one plane passing through the axis of rotation of the actuator so that rotation of the actuator shifts an adjacent structure in a direction transverse to the actuator's axis of rotation. For instance, the actuator may be mounted adjacent to a spinal rod in a manner in which operating the actuator will shift the spinal rod transversely, clamping the first spinal rod against another structure in the rod receiving device. In one aspect, the actuator may shift the spinal rod transversely into engagement with an end of the cross rod or a clamp device attached to the cross rod, locking both the spinal rod and cross rod in place within the rod receiving device.

In another aspect, the connecting assembly may include first and second rotatable actuators that form helical cam members. A helical cam member is capable of moving a spinal rod linearly in a direction parallel to the axis of rotation of the cam member. By operating the helical cam members, spinal rods can be drawn or driven into the rod receiving devices, following the helical surface conformation of the cam member shank as it is rotated within the rod receiving devices. As the spinal rods are drawn into position, the spinal rods may contact adjacent surfaces, such as the ends of the cross rod, thereby locking the ends of the cross rod with respect to the rod receiving devices.

Advantageously, the actuator members may be comprised of a material that is harder than the material that makes up the spinal rod. For instance, if the spinal rods are made of titanium, actuators formed from cobalt-chromium may be provided to lock the rods in place. It has been found that actuators of harder materials provide greater locking force than those made of softer materials, and that actuators made of material harder than the material of the spinal rods that they engage provides an especially strong locking force.

The rod receiving devices and/or actuators may include detent mechanisms in order to bias the actuators in an unlocked or locked position. For instance, a detent mechanism may be provided comprising a ridge or groove on the actuator that engages a corresponding ridge or groove on the rod receiving device to hold the actuator in an unlocked position until the surgeon provides sufficient force to overcome the biasing action of the detent mechanism and initiate locking. Similarly, a ridge, groove, or other structure may be provided at a different position on the rod receiving device to engage a corresponding structure on the actuator when the actuator is rotated or shifted into a locked position, biasing the actuator against movement back to the unlocked position.

Advantageously, a structure forming a hard stop may also be provided so that the actuator has a predetermined locked position. An actuator with a predetermined locked position provides a surgeon with certainty, since it is known that the device is locked when the actuator is rotated by a predetermined amount. Without a predetermined locked position, for instance when set screws are used as securing devices and tightened until a locking force is applied and the screw is fully engaged with its target, the surgeon must determine whether or not the set screw "feels" secured. This may result in a failure to lock the device or accidental over-torquing. An actuator with a set locked position also avoids the potential for cross-threading, another problem also associated with set screws. Therefore, unwanted stress and physical damage to the rod, connecting device, and the actuator itself are minimized by providing a preset locked position. In addition, the predetermined locked position is especially useful in MISS applications, where the surgeon often cannot see the implant.

In minimally invasive surgical systems for connecting spinal rods, a connecting assembly comprising two rod receiving devices connected by a cross rod may be implanted through a small incision, with or without an elongate guide tube or docking sleeve. The connecting assembly preferably has at least one seat for receiving a spinal rod, and at least one actuator member. If a guide tube is used, any tools used to manipulate the actuator or other portions of the assembly should be adapted to fit through the tube in order to operate the actuator member. Since the view through the guide tube is ordinarily obstructed by the tool, a stop may be provided to keep the tool from turning or otherwise operating the actuator member by more than a first predetermined amount so that the assembly need not be inspected to determine if the actuator has been properly manipulated.

In one form, the connecting assembly, or one of the rod receiving devices of such an assembly, is inserted into the body in a MISS surgical procedure. A relatively small incision is formed at a surgical site adjacent a first spinal rod. A guideway is confined through the small incision in order to form a guide to the site of implantation, through which the assembly and tools used to manipulate the connecting assembly may pass. A spinal rod at the site of implantation is engaged with a seat of the connecting assembly, and an actuator of the assembly is manipulated using a tool passing through the guideway. Preferably, the actuator is moved to a first predetermined position to secure the rod, and restricted from moving beyond the first predetermined position. The actuator may also have further predetermined positions. In one form, the actuator is rotated to a first predetermined rotary position, where the assembly is loosely secured to the rod so that the cross rod or other portions of the assembly may be adjusted, and then rotated to a second predetermined rotary position effective for fixing the connecting assembly against movement along the spinal rod.

The assembly may be designed so that movement of the actuator to a predetermined position generates tactile or even audible feedback to the surgeon to indicate when the predetermined position has been reached, for instance by providing a protrusion and/or recess on the actuator, the rod receiving device to which the actuator is mounted, or both.

In order to allow the rod receiving devices to be shifted linearly toward and away from each other to adjust the length of the connecting assembly, one of the rod receiving devices may contain a bore or cavity to slidably receive the cross rod. The cross rod may be shifted axially to an adjusted depth within the bore to lengthen or shorten the assembly. In order to lock the cross rod at a selected adjusted depth, a clamp member may be provided that will clamp against and immobilize the cross rod when one of the actuator members is operated. The clamp member may be disposed within the bore, and in one embodiment forms a compressible sleeve that surrounds a portion of the cross rod. The bore may be tapered in order to cause compression of the clamp member as it advances through the bore. The clamp member may include one or more slits in order to allow compression about the cross rod. The clamp member may also be formed from a deformable or elastic material that will compress onto the cross rod when sufficient pressure is applied by the actuator member. In one aspect, the clamp member may be cuneately shaped, for instance conical, in order to facilitate compression of the clamp member as it is moved into engagement with the inner surface of the bore.

BRIEF DESCRIPTION OF THE DRAWINGS

FIG. 2 shows two different embodiments of cross rods that may be pivotably received in a first rod receiving device and slidably received in a second rod receiving device.

FIG. 3 demonstrates the pivotal movement of one of the rod receiving devices about an end of the cross rod.

FIGS. 12a-12c demonstrate different types of actuator members for use in the transverse connector apparatus.

DETAILED DESCRIPTION OF THE PREFERRED EMBODIMENTS

Figure 1:
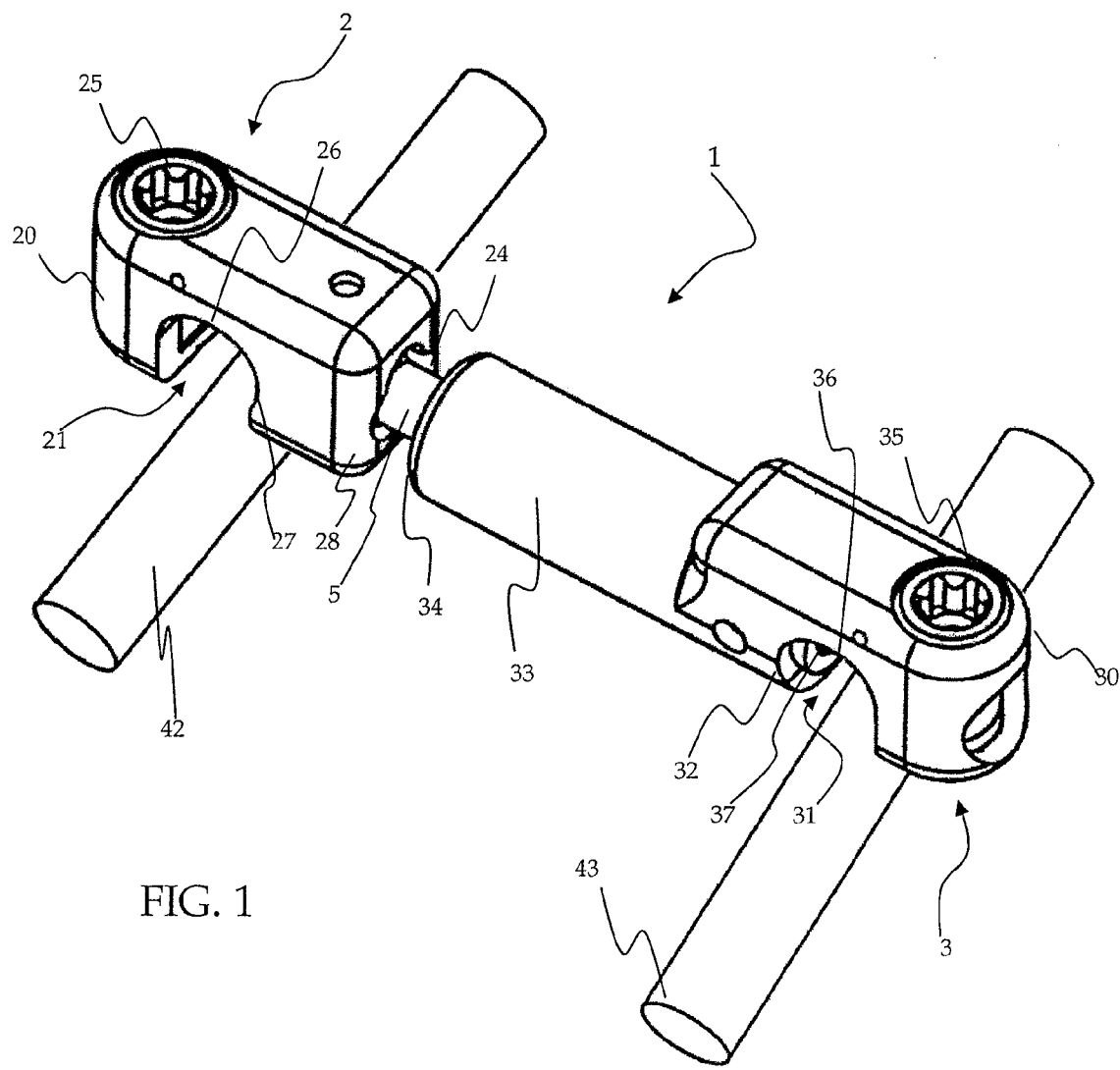
FIG. 1 shows a perspective view of an embodiment of the transverse connector assembly.

One embodiment of a transverse connecting assembly 1 for connecting two spinal rods 42 and 43 is shown in perspective by FIG. 1. The connecting assembly 1 comprises a first rod receiving device 2, a second rod receiving device 3, and a cross rod 5.

The first rod receiving device includes a rod receiving body 20 with a U-shaped recess 21 for receiving a spinal rod and a lateral opening 24 for receiving the cross rod 5. The recess 21 has an arcuate upper surface 26 and forms a seat configured to engage the surface of the spinal rod 42. A rotatable actuator 25 is disposed in the rod receiving body 20 adjacent to the recess 21. A side opening 24 in the side wall 28 of the body is sized so that the cross rod 5 may pivot. The opening 24 may be configured to permit pivoting of the cross rod 5 in one or more directions. Preferably, the cross rod 5 may pivot 360 degrees in the opening 24. In order to secure the first rod receiving device 2 to the spinal rod 42, the arcuate seat surface 26 is seated on the spinal rod 42 and the actuator 25 is rotated to shift the spinal rod 42 slightly toward the opposite lateral wall 27 of the recess 21, locking the rod in place.

Advantageously, in one form the rod receiving device 2 may be designed so that operation of the actuator 25 simultaneously secures the spinal rod 42 and a first end of the cross rod 5. For instance, the lateral opening 24 may open into the recess 21 in the rod receiving body 20. Shifting of the spinal rod 42 towards the lateral surface 27 causes the rod 42 to bear against the end of the cross rod 5 in order to lock the cross rod 5 against a lateral wall 28 of the body 20. Locking of the cross rod end is made possible by providing an abutment surface at the end of the rod configured to bear against an interior surface of the lateral wall 28 of the rod receiving device. The abutment surface on the cross rod may be in the form of an enlarged end, a removable collar, a pin connected transversely through the end of the cross rod 5, or other structures capable of bearing against the side wall 28 to prevent the cross rod from completely exiting the side opening 24.

The second rod receiving device 3 comprises a rod receiving body 30 having a recess 31 for receiving a spinal rod 43 and a rod receiving section 33 having a bore 37 that extends from its proximal end 32 to its distal end 34. The bore 37 axially receives the cross rod 5 so that the cross rod may be shifted axially to variable depths within the cross rod receiving portion 33. The bore 37 opens into the U-shaped recess 31 in the body of the device 30. The recess 31 has an arcuate upper surface 36 that forms a seat configured to engage the surface of the spinal rod 43. A rotatable actuator 35 is disposed in the rod receiving body 30 adjacent to the recess 31.

The actuator 35 disposed in the body 30 is operated to secure the spinal rod 43 in the U-shaped recess 31. Advantageously, the rod receiving device 3 may be designed so that operation of the actuator 35 simultaneously secures the spinal rod 43 and an end of the cross rod 5. When the spinal rod 43 is situated in the recess 31, rotation of the actuator 35 shifts the rod 43 toward the proximal end 32 of the cross rod receiving portion 33. In order to lock the cross rod 5 in the cross rod receiving portion 33, a clamp member is provided that may be disposed within the cross rod receiving portion 33 to engage the cross rod 5. Shifting of the spinal rod 43 towards the cross rod receiving portion 33 causes the spinal rod 43 to bear against an exposed surface of the clamp member located in the bore 37, forcing the clamp member to bear against the cross rod and fix it in place within the bore 37. The bore 37, clamp member, recess 31, spinal rod 43, and rotatable actuator 35 are sized and configured so that rotation of the actuator 35 tightly compresses the rod 43 against the clamp device, which in turn compresses against the interior of the bore 37, so that the spinal rod is tightly clamped between the actuator 35 and clamp device, and the clamp device is tightly clamped between the spinal rod 43, bore 37, and cross rod 5, thus locking both the spinal rod 43 and cross rod 5 in place.

The length of the cross rod receiving portion 33 of the second rod receiving device 3 may be selected to increase or decrease the adjustability of the assembly length. Providing a longer cross rod receiving portion 33 will provide a longer bore through which to shift the cross rod 5, allowing for greater extension. Providing a shorter receiving portion 33 will permit less extension by limiting the axial travel of the cross rod 5. However, a shorter receiving portion 33 will leave more of the cross rod 5 exposed, allowing a surgeon to bend the cross rod 5 in order to traverse spinal processes, other connectors, and other obstacles that may be present at the site of implantation. Alternatively, the receiving portion 33 may be made of a bendable material and configured so that the surgeon may bend both the receiving portion 33 and the cross rod 5.

FIG. 2 shows two different versions of the cross rod, 5a and 5b. The first cross rod 5a comprises a first rod end 8a, a shaft 9a, and a spherical pivot end 6a. The spherical pivot end 6a is disposed in the first rod receiving device 2 so that the shaft portion 10a of the cross rod protrudes from the lateral opening 24 of the rod receiving device. A first spherical or arcuate abutment surface 7a of the cross rod 5a engages a spinal rod when the spinal rod is shifted laterally by the action of the rotatable actuator member 25. A second spherical or arcuate abutment surface 9*a* engages the interior surface of the lateral wall 28 of the rod receiving device 2 when the spinal rod is shifted into engagement with the first abutment surface 7*a*. The engagement between the spinal rod and the first abutment surface 7*a* and between the second abutment surface 9*a* and the lateral wall 28 is tight enough to create a locking force that fixes the cross rod 5*a* against pivotal movement about the spherical end 6*a* and further prevents the spinal rod from exiting the U-shaped recess 21 of the rod receiving device. Prior to locking engagement between the spinal rod and spherical end 6*a* of the cross rod 5*a*, the cross rod 5*a* is permitted to rotate in two or more directions when the spherical portion 6*a* is disposed within the receiver body 20 and the shaft 10*a* extends from the lateral opening 24 in the body 20.

Alternatively, a second form of cross rod 5*b* may be provided with a disc shaped end 6*b*. The disc shaped end 6*b* is more limiting of the pivotal movement of the cross rod than the spherical end 6*a*. As with the first form of the cross rod, the second form with the disc-shaped end portion contains an opposite rod-shaped end 8*b* and a shaft 10*b* connected to the pivot end 6*b*. The disc shaped pivot end 6*b* is disposed in the first rod receiving device 2 so that the shaft portion 10*b* of the cross rod protrudes from the lateral opening 24 of the rod receiving device. A first arcuate abutment surface 7*b* of the cross rod 5*b* is engaged by a spinal rod when the spinal rod is shifted laterally by the action of the rotatable actuator member 25. A second arcuate abutment surface 9*b* engages the interior surface of the lateral wall 28 of the rod receiving device 2 when the spinal rod is shifted into engagement with the first abutment surface 7*b*. The engagement between the spinal rod and the first abutment surface 7*b* and between the second abutment surface 9*b* and the lateral wall 28 is tight enough to create a locking force that fixes the cross rod 5*b* against pivotal movement about the spherical end 6*a* and further prevents the spinal rod from exiting the U-shaped recess 21 of the rod receiving device. Prior to locking engagement between the spinal rod and spherical end 6*b* of the cross rod 5*b*, the cross rod 5*b* is permitted to pivot back and forth with the pivot end 6*b* disposed within the receiver body 20 and the shaft 10*a* extending from the lateral opening 24 in the body 20. Detents may be placed on the disc-shaped portion 6*b* or on the interior of the rod receiving device 20 in order to provide predetermined pivot positions for the cross rod 5*b*.

The pivot end of course may take other forms, and may even be eliminated in some cases. If pivotal movement is not necessary, or if pivotal movement is provided at the other end of the connector, the cross rod 5 may be formed integral with the rod receiving member 2.

A pin may be inserted into an opening 11 in the rod receiving body 20 and into engagement with the pivot end 6*a* or 6*b* of the cross rod in order to retain the cross rod in the rod receiving device 20 and to limit the pivoting of the pivot end of the cross rod. The pin may be press fitted into the opening 11, or alternatively may be secured in the opening using solder, cement, adhesive, or the like.

When the pivot end is received in the first rod receiving device 2 and prior to locking, the device 2 may pivot with respect to the other rod receiving device 3, as shown in FIG. 3.

Figure 4:
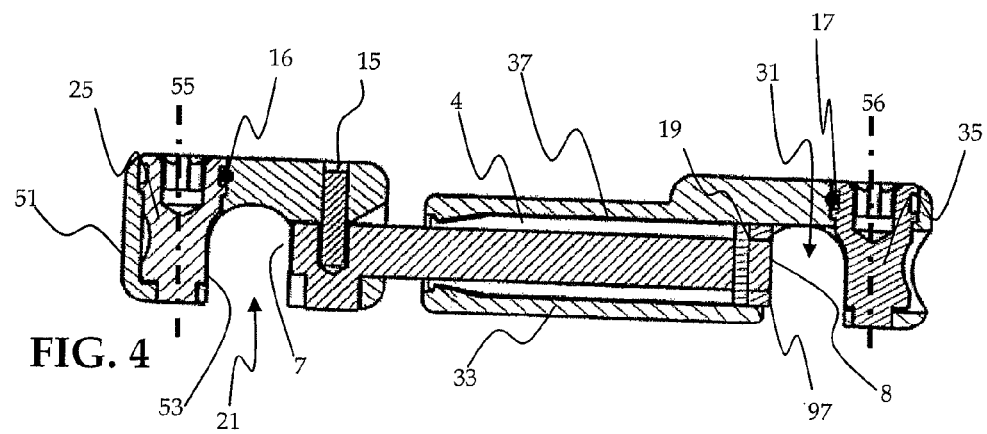
FIG. 4 shows a cross-sectional view of the transverse connector apparatus with cam actuator members in an unlocked position.

A cross section of the connecting assembly, as in FIG. 4, reveals the cross rod 5 extending between two U-shaped rod-receiving recesses 21 and 31. The pivot end 6 of the cross rod 5 is held in a cavity adjacent and open to the recess 21 by a pin 15, which prevents the pivot end from backing out of the cavity into the recess 21 or escaping fully from the rod receiving body 20. The pin 15 holds the pivot end 6 loosely enough, however, that the pivot end 6 may be forced into contact with the adjacent lateral wall 28 to fix the pivot portion 6 against movement relative to the rod receiving body.

The opposite end 8 of the cross rod is disposed within a clamp member 4, which in turn is disposed within the bore 37 of the cross rod receiving portion 33. The recesses 21 and 31 adjacent to the cross rod receive spinal rods that may be shifted laterally into locking engagement with an abutment surface 7 of the rod and an abutment surface 97 of the clamp member, respectively. A retaining structure such as a retaining pin 19 may be provided to retain the cross rod 5 within the clamp member 4. The retaining pin 19 is sized to allow movement within the clamp member but prevent exit of the cross rod 5 through one or both openings of the clamp member.

Figure 5:
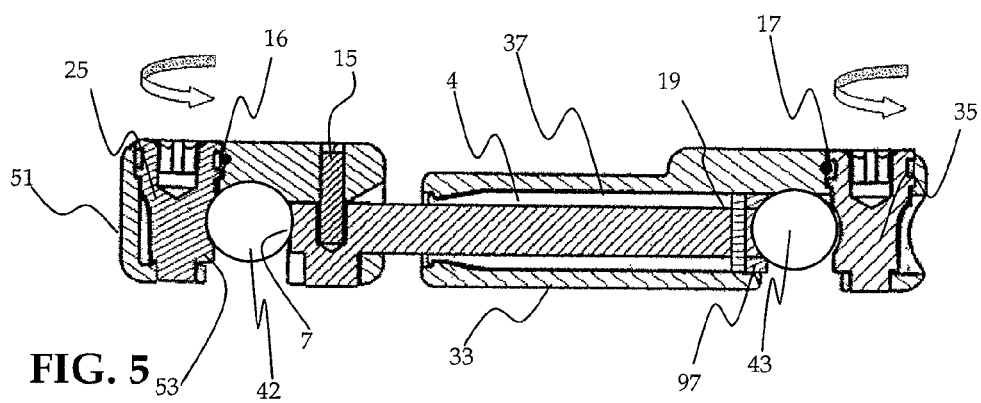
FIG. 5 shows a cross-sectional view of the transverse connector apparatus with cam actuator members rotated to a locked position.

In order to effect lateral shifting of the spinal rods within recesses 21 and 31, the rotatable actuator members 25 and 35 may be formed so that they are rotationally asymmetric, having locking surfaces 51 and 52 that are located further from their respective axes of rotation 55 and 56 than unlocking surfaces 53 and 54. Locking of the assembly is caused by rotating the actuators 25 and 35 so that their locking surfaces 51 and 52 are presented to the adjacent rod-receiving recesses 21 and 31, respectively, as shown in FIG. 5, reducing the width of the recesses. By reducing the effective width of the recesses 21 and 31, spinal rods seated in the recesses are forced laterally into engagement with either the pivot end 6 of the cross rod or the clamp 4 surrounding the cross rod 5.

Figure 17:
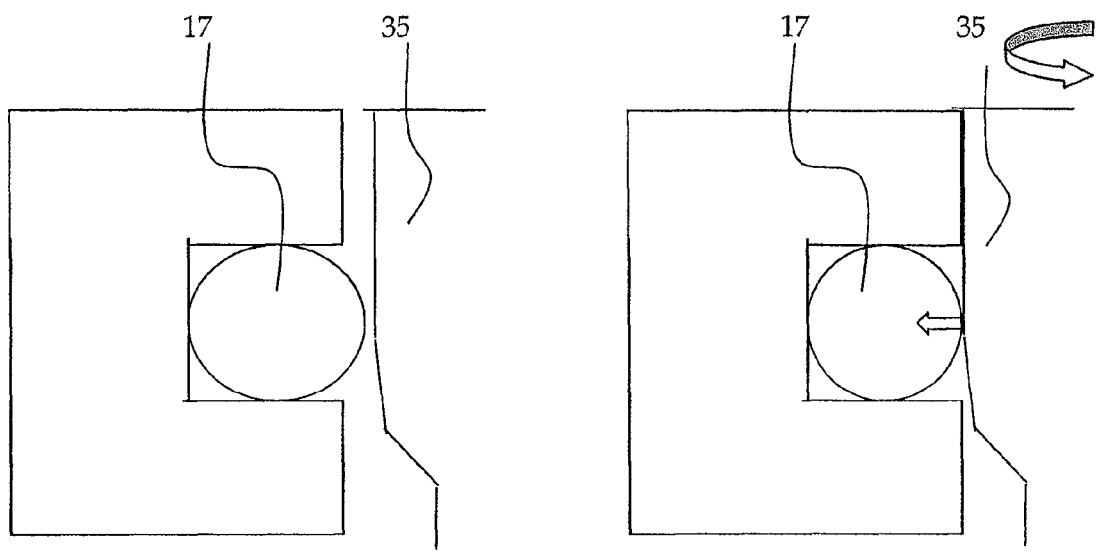

Biasing mechanisms may be provided in order to maintain the actuators in an unlocked and/or locked position. In FIGS. 4-7, the biasing mechanism is shown in the form of elastically deformable detent pins 16 and 17. The upper portions of the actuators may be given asymmetric surfaces so that rotation of the actuators out of the unlocked position engages and deforms one of the pins, as demonstrated in FIG. 17, requiring the surgeon to apply sufficient torque to deform the pin in order to rotate the actuator. As shown in FIG. 17, rotation of the cam member 35 engages a deformable pin, 17, making rotation of the cam member more difficult. Likewise, the actuators may be configured so that rotating the actuator into and out of the locked position requires overcoming a detent. In one form, the same biasing mechanism may be used to bias the actuators in both the locked and unlocked positions.

Figure 6:
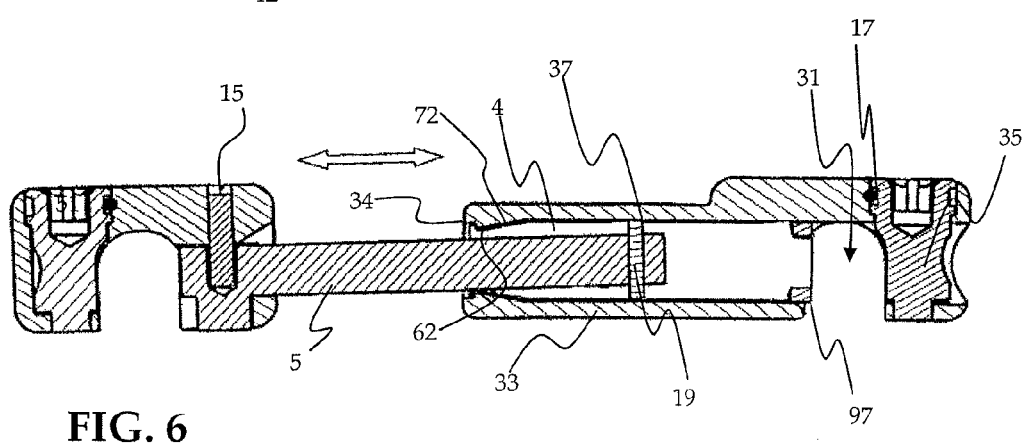
FIG. 6 demonstrates the lengthening of the transverse connector apparatus by shifting the cross rod axially through a bore in one of the rod receiving devices.

Telescoping extension of the cross rod 5 and cross rod receiving portion 33 allows the surgeon to alter the span between rod receiving devices 2 and 3, as shown in FIG. 6. The cross rod may shift axially through clamp member 4 that is disposed in the bore 37 of the rod receiving portion 33. The clamp member 4 is held within the bore 37 by a lip 61 formed at one end that prevents movement of the clamp member in the direction of the rod receiving recess 31 past a predetermined point. Movement of the clamp in the opposite direction is limited by the interaction of a tapered surface 62 on the clamp member and a tapered surface 72 of the bore. A retaining pin 19 inserted into the cross rod 5 prevents the cross rod from fully exiting the clamp member 4, preventing accidental disassembly of the connector prior to locking.

Figure 7:
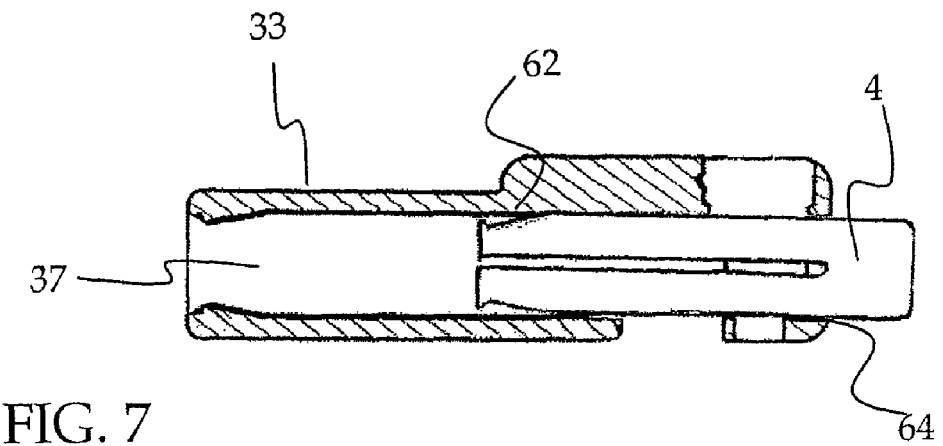
FIG. 7 demonstrates insertion of a clamp member into a rod receiving body.

During assembly of the transverse connector shown in FIG. 7, the clamp member 4 is inserted through a lateral opening 64 of the rod receiving device 3 and into the cross rod receiving portion 33. The clamp member 4 shown in FIG. 7 forms an elongate sleeve with an axial passage, although other types of clamp members may be employed. The clamp member need not fully surround the cross rod 5, as long as it is capable of clamping against the cross rod 5 as it travels through the bore 37. Prior to positioning the actuator member 35 in the rod receiving body 30, a clear passage exists from the lateral opening 64 to the bore 37. After insertion of the clamp member 4, the actuator member 35 may be inserted into the rod receiving body 35, blocking the lateral opening 64. As the clamp member 4 is inserted into the bore 37, the tapered surface 62 of the clamp will engage a corresponding tapered surface 72 of the bore. Further axial translation of the clamp member 4 against the tapered surface 72 of the bore causes collapse or compression of the clamp member 4. It will be understood that the clamp member 4 need not be tapered in order to compress when driven against the tapered surface 72 of the bore. Prior to insertion of the cross-rod 5 into the axial passage of the clamp, the clamp 4 may be compressed to an extent that the lip 61 on the clamp member passes through the narrow portion 65 of the bore 37. After the lip 61 has cleared the narrow portion 65 of the bore 37, the clamp 4 is allowed to expand again. The configuration of the lip 61 of the clamp and the narrow portion 65 of the bore allows for some axial movement of the clamp in the bore, but prevents the clamp 4 from fully retreating from the bore 37. The clamp member 4 is prevented from exiting the opposite end of the bore 37 because the clamp member 4 is incapable of compressing enough to fully exit the narrow portion 65 of the bore. Once the clamp member 4 is properly situated in the bore 37, the cross rod 5 may be inserted into the clamp member 4.

Figure 8A:
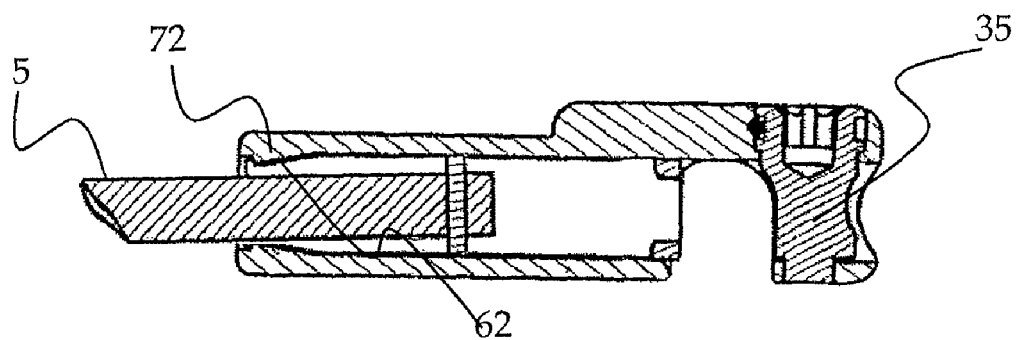
FIG. 8 is a cross sectional view demonstrating the operation of the clamp member to fix the cross rod at an adjusted depth within the bore.
Figure 8B:
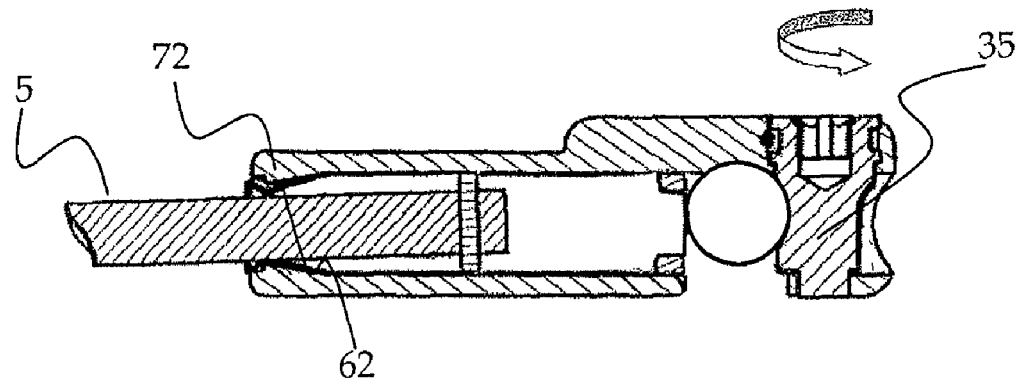

Operation of the clamp member 4 is controlled by the rotatable actuator member 35, as shown in FIG. 8. The rotatable actuator member 35 includes a locking surface 52 which, when presented to a spinal rod 43 located in the rod receiving recess 31, forces the spinal rod 43 toward the mid-line of the assembly and against an abutment surface 63 of the clamp member 4. Full rotation of the actuator member 35 to a locked position drives the taper 62 of the clamp into engagement with the taper 72 on the bore to an extent that the clamp 4 is compressed against the cross rod 5 with sufficient force to fix the cross rod against linear or rotational movement within the bore 37.

Figure 9A:
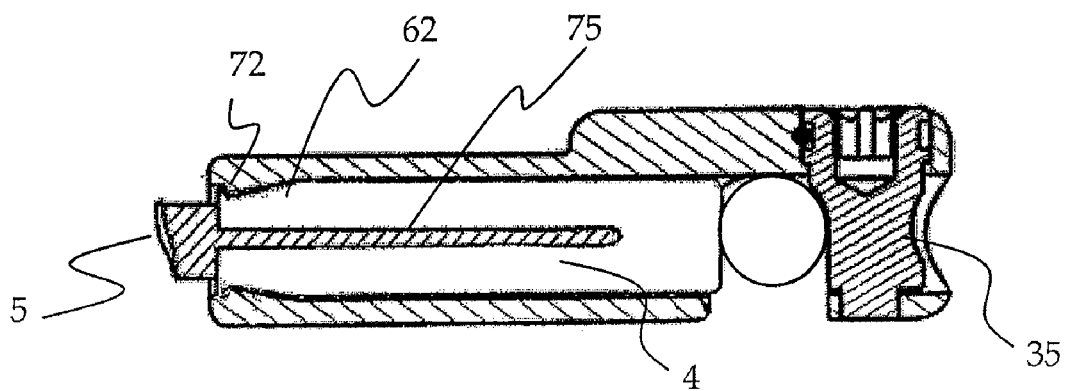
FIG. 9 is an additional view demonstrating the operation of the clamp member to fix the cross rod at an adjusted depth within the bore, showing the exterior of the clamp member within a cross section of the rod receiving device.
Figure 9B:
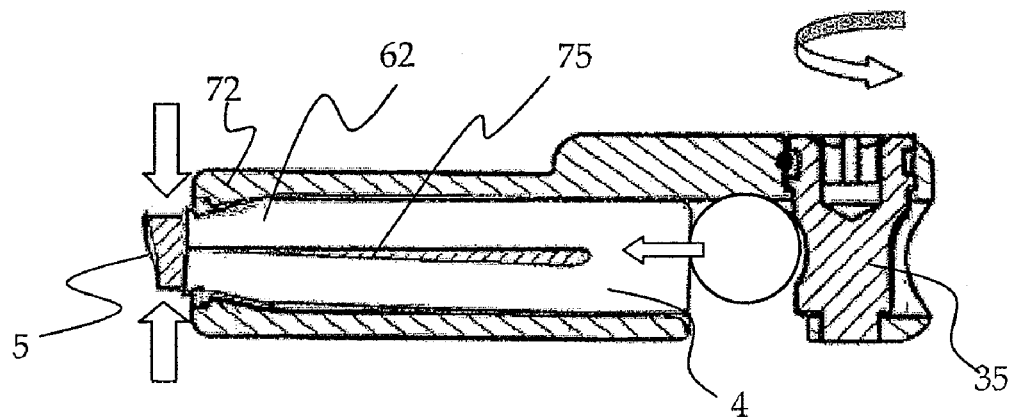

The clamp member 4 may be formed as a sleeve containing one or more slits 75 that allow at least a portion of the sleeve to compress radially, as shown in FIG. 9. As the end of the clamp member is driven against the taper 72 of the bore, the clamp arms 76 on either side of the slits 75 are compressed radially, narrowing the slits 75 and engaging the surface of the cross rod 5 to lock it in place. The clamp need not contain slits if it is formed of a sufficiently deformable material to compress against the cross rod with a locking force when driven through the bore. In addition, the clamp member may be provided in the form of a simple wedge or combination of wedges driven along one or more sides of the cross-rod to lock the rod within the bore. Other variations of sliding clamp mechanisms are also possible.

Figure 11:
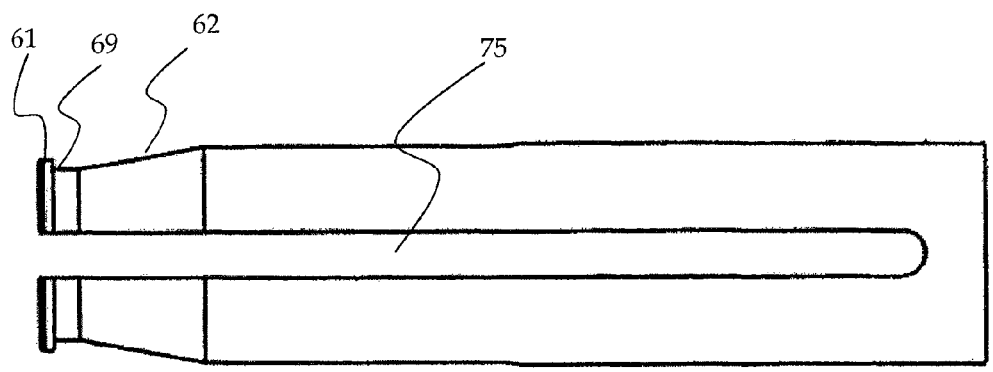
FIG. 11 shows an external view of one type of clamping member having a slit running down a substantial portion of its length.
Figure 10:
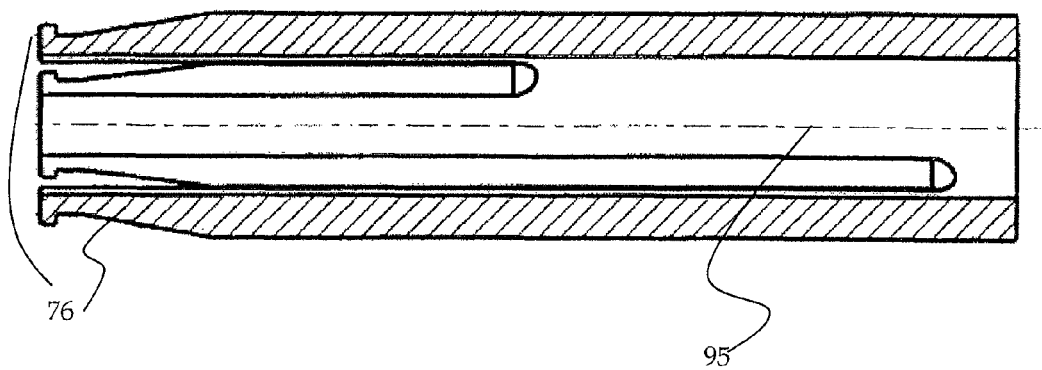
FIG. 10 shows a cross sectional view of one type of clamping member containing two different sets of slits, both for allowing compression of the clamp member and for guiding a cross rod for axial shifting in the clamping member.

The sleeve-type clamp member is shown in detail in FIGS. 10 and 11. Multiple axial slits of varying lengths may be provided to allow arms to compress radially, as shown in cross section in FIG. 10 and from the exterior in FIG. 11. As shown in FIG. 11, a narrow translating surface 69 is provided between the tapered surface 62 and the lip 61. The translating surface may translate through the narrow portion 38 of the bore 37 (FIGS. 8-9), which is too narrow to accommodate the lip 61 or most of the tapered clamp surface 62 when the cross rod is disposed within the axial passage 95 of the clamp member.

The actuators that drive locking of the assembly may be of any type that cause shifting of the spinal rods sufficient to lock the rods against a surface of the cross rod or another surface that will effect clamping of the cross rod. Examples of actuator members are shown in FIG. 12. In one embodiment, shown in FIG. 12a, the actuator is an asymmetric rotatable member 25. The rotatable member has an axis of rotation 55 a locking surface 51 and an unlocking surface 53. A recess 91 in one end of the member is configured to receive an instrument for effecting rotation of the actuator member. The locking surface 51 is located a distance (a) from the axis of rotation 55 that is greater than the distance (b) of the unlocking surface 53 to the axis 55. When a spinal rod is positioned adjacent the unlocking surface 53 and the actuator is rotated, the spinal rod will be shifted laterally away (radially outward) from the axis of rotation 55 as the locking surface 51 is brought into engagement with the spinal rod.

Engagement between the locking surface may cause some elastic or inelastic deformation of the actuator and/or the spinal rod as the spinal rod is compressed between the locking surface 51 and any structure located on the opposite side of the actuator. As shown, the locking and unlocking surfaces of the actuator 25 are offset from one another by 180 degrees about the axis of rotation 55, but the locking and unlocking surfaces may be arranged at any angular distance from one another so that less or more rotation is required to move from an unlocked to a locked position. For instance, the actuators may be configured so that they are rotated 90 degrees or less from an unlocked to a locked position.

Preferably, the actuator is formed of a material that is harder than the material that makes up the spinal rod, since this has advantageously been discovered to produce a greater locking force between the actuator and spinal rod. For instance, since spinal rods are commonly formed from titanium, a cobalt-chromium actuators may be provided rather than titanium actuators in order to increase the holding strength of the connecting assembly.

A ridge, flat, or other structure may also be provided on the actuator that acts as a hard stop to prevent rotation of the actuator past a preset limit when the actuator is disposed within a rod receiving body. In this way, the surgeon will know that rotation of the actuator by a predetermined amount achieves the locking position, eliminating guesswork and the danger of overtorquing. Preferably, the preset locking position is achieved by rotating the actuator 180 degrees or less, more preferably 90 degrees or less, to conserve time and energy. A predetermined locking position is particularly advantageous in applications where the surgeon will not be able to clearly view the locking mechanism during implantation such as in MISS applications.

Another embodiment of a rotatable actuator is shown in FIG. 12b. The rotatable actuator 80 has an axis of rotation 79, an unlocking surface 77 and a locking surface 78. The locking surface 78 forms an arcuate surface and is generally located further from the axis of rotation 79 than the opposite unlocking surface 77. The unlocking surface 77 forms an arcuate face to loosely receive a spinal rod located in a space adjacent the actuator, while the locking surface 78 will tightly receive a spinal rod located in the same adjacent space.

FIG. 12c shows yet another rotatable actuator 81 forming a helical cam member having an axis of rotation 82 and a helical shank 83. As the actuator 81 is rotated about its axis 82, a spinal rod engaged with the surface of the helical cam surface of the shank 83 will be shifted along the helical shank surface. The spinal rod may be drawn upward or downward along the shank surface, depending on the direction of rotation. When such a helical cam member is mounted in an assembly of the type shown in FIGS. 1-9, wherein the rod receiving devices include arcuate seats adjacent the rotatable actuators, the helical surfaces of the cam members will cause shifting of the spinal rods along the helical shank surfaces into the arcuate seats as the cam member is rotated.

In addition, the actuators may be of a non-rotatable type. For instance, the actuators may comprise pivotable or slidable actuators that shift to provide a locking force against an adjacent spinal rod.

Figure 13:
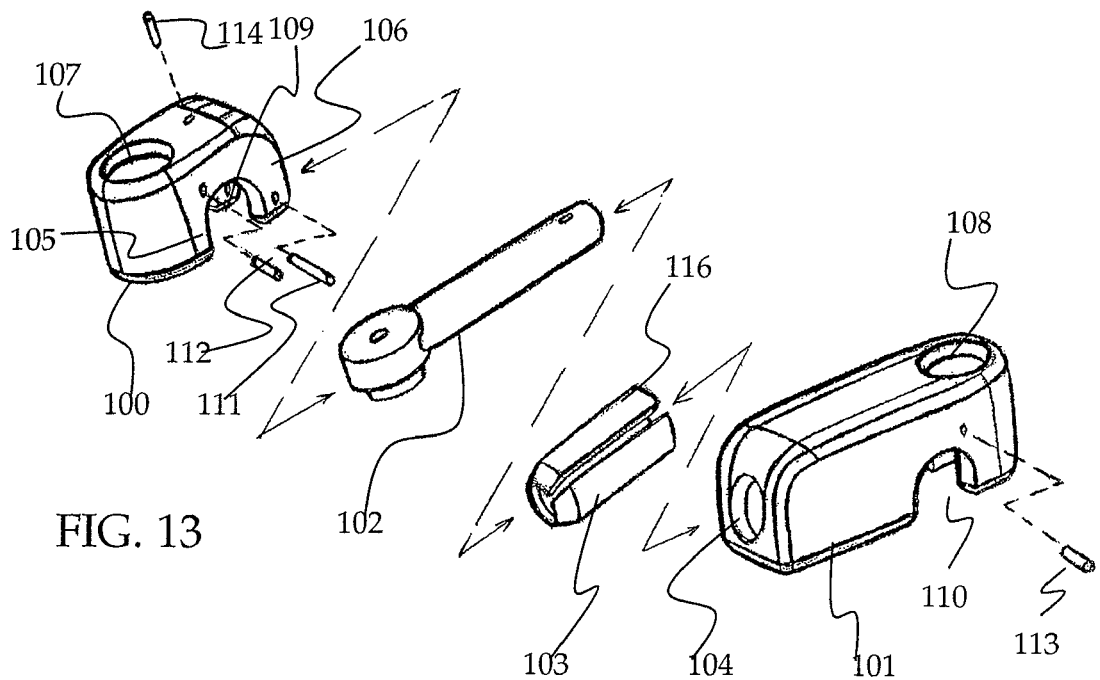
FIG. 13 shows an alternative transverse connector assembly with a cross rod having a cylindrical joint at one end for pivoting in at least two directions.
Figure 14:
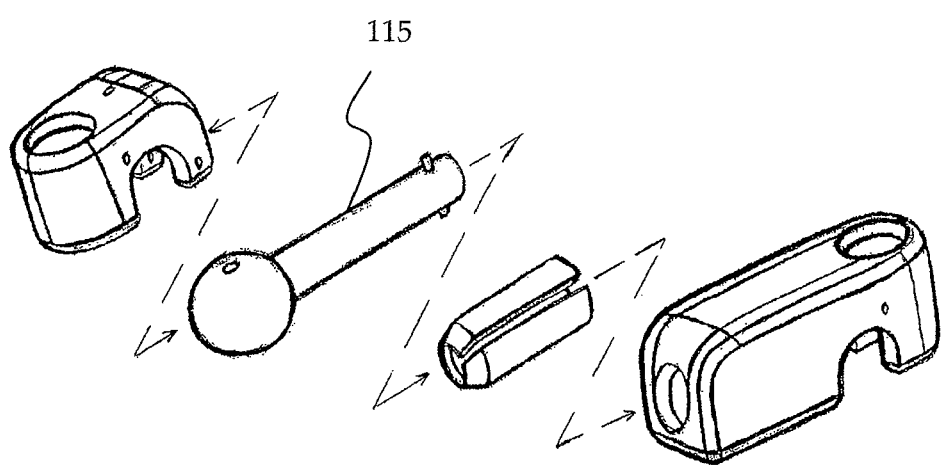
FIG. 14 shows another alternative transverse connector assembly with a cross rod having a spherical joint at one end for pivoting in any number of directions.

FIGS. 13 and 14 show additional embodiments of transverse connector assemblies. Similar to the embodiments described above, the assemblies include rod receiving devices 100 and 101 and a compressible clamp member 103. The clamp member 103 is formed as a locking sleeve with a single axial slit 116 running the entire length of the sleeve. A cross rod 102 or 115 may be pivotably received in one rod receiving device 100 and slidably received in a bore 104 of the other rod receiving device 101. The devices contain recesses forming seats 109 and 110 for seating atop spinal rods. Openings 107 and 108 transverse to the cross rod and adjacent to the seats 109 and 110 receive rotatable actuators as described elsewhere herein. Pins 112 and 113 may be inserted to retain the actuators, and to provide a detent mechanism as described elsewhere herein. A pivot pin 114 may be used to provide a fixed pivot axis for the cross rods 102 and 115. Alternatively, the pivot pin may be eliminated or removed to allow free rotation of the pivot end, especially for cross rod 115, which has a substantially spherical pivot end for multi-angle pivotal movement. The connecting assemblies operate in a similar manner as those described above.

Figures 15, 16:
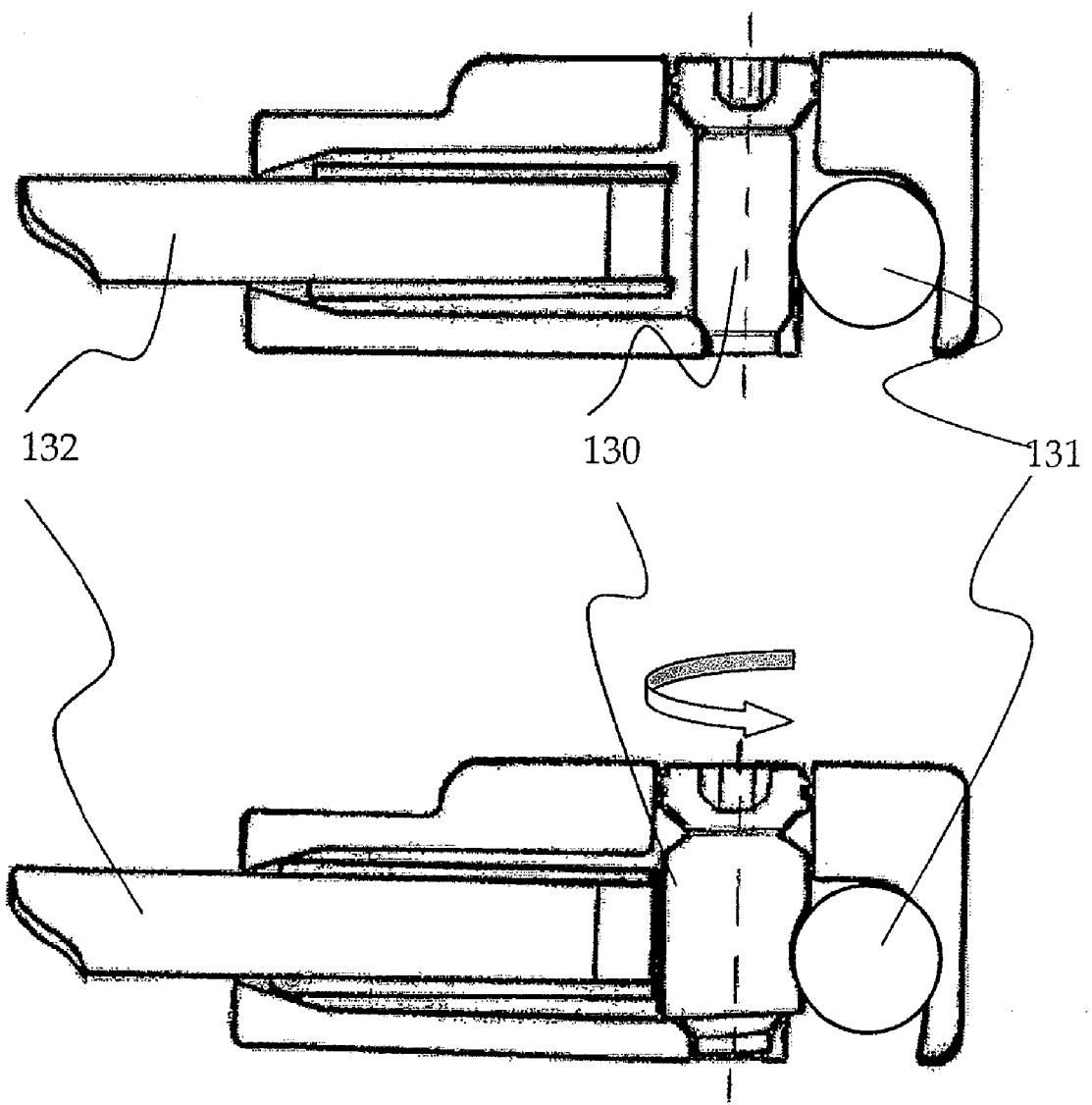
FIG. 15 shows an alternative rod receiving device including a rotating actuator mounted intermediate the cross rod and spinal rod.
FIG. 16 demonstrates locking of the alternative rod receiving device including a rotating actuator mounted intermediate the cross rod and spinal rod FIG. 17 demonstrates detail of a detent mechanism for biasing or stopping rotation of a cam member.

In yet another embodiment, the actuator mechanism is disposed intermediate the spinal rod and the cross rod. Rotation of the actuator mechanism provides radially outwardly directed forces for locking a spinal rod and/or cross rod. In the embodiment shown, the intermediate actuator is effective for simultaneously locking the spinal rod and an end of the cross rod, as shown in FIGS. 15 and 16.

Embodiments of the transverse connecting assemblies that provide full locking of two spinal rods and a cross rod having multiple points of articulation by operating only two actuating members may be advantageously used in MISS operations. Since the actuating mechanisms are positioned close to the spinal rod seats, the assemblies are particularly advantageous in that the intermediate span of the cross rod need not be manipulated directly in order to effect locking thereof.

In MISS procedures, docking tubes may be inserted through small incisions in the skin and used to deliver the connector to the implantation site. In one form, the two rod connecting devices of the connecting assembly are inserted through docking tubes located on opposite sides of the spine, and then connected to each other subcutaneously. It is also possible to insert the entire assembly through a single tube, and then position the assembly onto implanted spinal rods. Once the assembly is seated on the spinal rods, the actuator members may be operated using an instrument that is extended through the docking tube to interact with the implanted assembly.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A connecting assembly for interconnecting spinal rods secured to spinal vertebrae, the connecting assembly comprising:

an elongate cross rod having a first cross rod end and a second cross rod end and a longitudinal axis extending between the first cross rod end and second cross rod end;

a first rod receiving device and a second rod receiving device each configured to receive a cross rod end and a spinal rod, the first rod receiving device configured to allow the first cross rod end received thereby to pivot with respect to the first rod receiving device, and the second rod receiving device configured to adjustably receive the second cross rod end so that an axial adjustable distance between the first rod receiving device and the second rod receiving device can be selected by axial adjustment of the cross rod therebetween;

a first rotatable actuator and a second rotatable actuator each associated with one of the first rod receiving device and the second rod receiving device, with the first rotatable actuator rotated to secure the first cross rod end to the first rod receiving device against pivoting relative thereto and the second rotatable actuator rotated to secure the second cross rod end to the second rod receiving device against axial shifting relative thereto so that the axial adjustable distance between the first rod receiving device and the second rod receiving device is fixed;

wherein the second rod receiving device includes an axially extending bore and a clamping mechanism located therein, the clamping mechanism operated by rotation of the second actuator to clamp the second cross rod end against axial movement;

the clamping mechanism comprising an elongate clamping sleeve that extends axially in the axially extending bore, with the second cross rod end and the axial bore being sized to allow the second cross rod end to be adjusted to different axial positions within the elongate clamping sleeve so that operation of the second rotatable actuator causes clamping of the second cross rod end against axial movement to fix the axial distance between the rod receiving devices to a selected axial distance therebetween.

2. The connecting assembly of claim 1 wherein the first cross rod end has a disc-shaped configuration received in the first rod receiving device for pivoting of the cross rod thereabout.

3. The connecting assembly of claim 1 wherein the first cross rod end has an arcuate surface received in the first rod receiving device for pivoting of the cross rod thereabout.

4. The connecting assembly of claim 3 wherein the first actuator has a cam surface configured so that rotation of the first actuator causes the cam surface to bear tightly against the spinal rod, which in turn bears against the first cross rod end arcuate surface to substantially fix the cross rod against pivoting.

5. The connecting assembly of claim 1 wherein surfaces of the sleeve are configured to cooperate with surfaces of the bore in the second rod receiving device to cause the sleeve to clamp onto the second cross rod end with axial shifting of the sleeve through the bore toward the first cross rod end, so that the sleeve contacts the second cross rod end at a majority of a circumference of the second cross rod end.

6. The connecting assembly of claim 1 wherein the second actuator has a cam surface configured so that rotation of the second actuator causes the cam surface to push the spinal rod and the sleeve in the bore toward the first cross rod end.

7. The connecting assembly of claim 1 wherein the first rotatable actuator is asymmetric with respect to at least one plane passing through its axis of rotation so that rotation of the first actuator member shifts one of the spinal rods in a direction transverse to the first rotatable actuator's axis of rotation, clamping a first spinal rod and the first end of the cross rod together within the first rod receiving device, and wherein the second rotatable actuator is asymmetric with respect to at least one plane passing through the axis of rotation so that rotation of the second actuator member shifts a second spinal rod in a direction transverse to the second rotatable actuator member's axis of rotation, forcing the second spinal rod into contact with the sleeve, thereby clamping the sleeve to the cross rod within the bore and preventing axial movement of the cross rod with respect to the second rod receiving device.

8. The connecting assembly of claim 1 wherein the first rod receiving device and second rod receiving device each include arcuate seats, the first rotatable actuator and second rotatable actuator each have a shank including a helical cam surface, and rotation of the first rotatable actuator and second rotatable actuator and the helical cam surfaces thereof causes the spinal rods to shift along the shanks and into engagement against the arcuate seats.

9. The connecting assembly of claim 1 wherein the first rotatable actuator and second rotatable actuator are made of a first material and the spinal rods are made of a second material, wherein the first material is harder than the second material.

10. The connecting assembly of claim 1 wherein the rod receiving devices each include a detent mechanism to bias the first rotatable actuator and the second rotatable actuator against rotation.

11. The connecting assembly of claim 1 wherein at least one of the first rotatable actuator and the second rotatable actuator contains a protrusion or groove to stop rotation of the first rotatable actuator or second rotatable actuator at a predetermined locked position.

12. A connecting assembly for interconnecting spinal rods secured to spinal vertebrae, the connecting assembly comprising:
 a first rod receiving device for receiving a first spinal rod, the first rod receiving device having an opening for receiving a first end of a cross rod and a first non-threaded actuator member rotatable about a first axis of rotation and having a predetermined locking position;
 a second rod receiving device for receiving a second spinal rod, the second rod receiving device having an opening for receiving a second end of the cross rod and a second non-threaded actuator member rotatable about a second axis of rotation and having a predetermined locking position;
 the cross rod pivotably connected to at least one of the rod receiving devices and slidably received in at least one of the rod receiving devices; and
 the first non-threaded actuator member configured to apply a locking force in a direction orthogonal to the first axis of rotation of the first non-threaded actuator member for shifting the first spinal rod in the same direction as the locking force is applied toward the first end of the cross rod in order to fix the first end of the cross rod within the first rod receiving device; and the second non-threaded actuator member configured to apply a locking force in a direction orthogonal to the second axis of rotation of the second non-threaded actuator member for shifting the second spinal rod in the same direction as the locking force is applied toward the second end of the cross rod in order to operate a clamping mechanism that fixes the second end of the cross rod against axial shifting within the second rod receiving device.

13. The connecting assembly of claim 12 wherein the first and second actuators are asymmetric so that rotation of the actuator from a first position to a second position shifts a spinal rod linearly toward an end of the cross rod in order to prevent the cross rod and spinal rod from moving with respect to the rod receiving device.

14. The connecting assembly of claim 12 wherein the first actuator is positioned directly adjacent the first spinal rod and the second actuator is positioned directly adjacent the second spinal rod.

15. The connecting assembly of claim 12 wherein the actuators are configured to stop at a predetermined locked position.

16. The connecting assembly of claim 12 wherein the first and second actuators are made of a first material and the spinal rods are made of a second material, wherein the first material is harder than the second material.

17. The connection assembly of claim 12 wherein the second rod receiving device contains a bore and a clamp device disposed within the bore, wherein the clamp device is shifted by one of the actuating members between a clamped position and an unclamped position.

18. The connecting assembly of claim 17 wherein the bore in the second rod receiving device is tapered toward an opening of the bore, and wherein the clamp device is formed from a resiliently deformable material that is compressed as the clamp device is shifted axially through the bore, clamping the cross rod in place.

19. The connecting assembly of claim 17, wherein the clamp device is cuneately shaped and clamps against the cross rod as the clamp device is shifted toward the opening of the bore in the second rod receiving device.

20. The connecting assembly of claim 12, wherein the connecting assembly has six degrees of movement when the first and second actuator members are each in an unlocked position, and wherein the connecting assembly has zero degrees of movement when the first and second actuator members are each in a locked position.

21. A method for interconnecting a first spinal rod that is secured to a spinal vertebra with a second spinal rod that is secured to the spinal vertebra, the method comprising:
 seating the first spinal rod in a first rod receiving device;
 seating the second spinal rod in a second rod receiving device;
 connecting the rod receiving devices with a cross rod;
 adjusting a distance between the first rod receiving device and the second rod receiving device by shifting the cross rod within at least one of the devices;
 shifting the first spinal rod and the second spinal rod toward each other in locking directions by rotating actuator members about axes that are transverse to the locking directions in which the first and second spinal rods are to be shifted in order to apply locking forces upon the spinal rods in the locking directions; and
 fully locking the first spinal rod, second spinal rod, and the cross rod via only rotation of the actuators that shift the first spinal rod and second spinal rod toward each other to substantially fix the spinal rods and cross rod against linear, rotational, and pivotal movement with respect to the first and second rod receiving devices.

22. The method of claim 21, further comprising rotating the actuator members in order to fully lock the first spinal rod, second spinal rod, and the cross rod.

23. The method of claim 22, further comprising rotating the actuator members to a predetermined locked position in order to fully lock the first spinal rod, second spinal rod, and the cross rod.

24. The method of claim 21, further comprising shifting the first and second spinal rods in directions generally parallel to the cross rod axis into contact with the cross rod in order to fully lock the first spinal rod, second spinal rod, and the cross rod.

25. The method of claim 21 further comprising:

forming a small incision at a surgical site adjacent a spinal rod and a spinal vertebrae;

extending an elongate tubular member through the small incision; and inserting one of the rod receiving devices through the elongate tubular member before seating the respective spinal rod in the rod receiving device.

26. The method of claim 25 wherein the actuator member of the rod receiving device is rotated using a tool that is adapted to fit through the elongate tubular member.

27. The method of claim 25 further comprising rotating an actuator member of the rod receiving device with a tool to a first predetermined rotary position for securing of the spinal rod and an end of the cross rod to the rod receiving device.

28. The method of claim 27 wherein turning the actuator member to the predetermined rotary position generates tactile feedback to a user turning the actuator member to indicate when the predetermined rotary position has been reached.

29. The method of claim 27 further comprising:

adjusting the cross rod while the actuator member is in the first predetermined rotary position; and turning the actuator member to a second predetermined rotary position in order to fully lock the spinal rod and the cross rod to the rod receiving device.

30. The method of claim 29 wherein turning the actuator member to the first predetermined rotary position generates tactile feedback to a user turning the actuator member to indicate when the predetermined rotary position has been reached.

31. A connecting assembly for interconnecting spinal rods comprising two rod receiving devices connected by an adjustable cross rod, wherein the rod receiving devices each include a seat for receiving a spinal rod and a non-helical actuator member located adjacent the seat, wherein the non-helical actuator member has an axis of rotation and is asymmetrical about the axis of rotation, and wherein the non-helical actuator is rotatable into engagement with one of the spinal rods without movement along the axis of rotation to shift one of the spinal rods toward the cross rod in a direction transverse to the axis of rotation for generating a locking force that fixes the cross rod against movement relative to the associated rod receiving device in a predetermined direction.

32. The connecting assembly of claim 31 wherein the locking force is directly applied by the spinal rod to the cross rod.

* * * * *